United States Patent [19]

Frost et al.

[11] Patent Number: 5,187,163

[45] Date of Patent: Feb. 16, 1993

[54] ANTI-VIRAL COMPOUNDS, DOSAGE FORMS AND METHODS

[75] Inventors: Phillip Frost, Miami Beach; Jack Fishman, Miami; Elliot Hahn, North Miami Beach, all of Fla.; Jing J. Lu, Terre Haute, Ind.

[73] Assignee: Baker Norton Pharmaceuticals, Inc., Miami, Fla.

[21] Appl. No.: 825,823

[22] Filed: Jan. 28, 1992

Related U.S. Application Data

[63] Continuation of Ser. No. 638,335, Jan. 8, 1991, abandoned, which is a continuation-in-part of Ser. No. 319,680, Mar. 7, 1989, abandoned, which is a continuation-in-part of Ser. No. 122,736, Nov. 19, 1987, abandoned, which is a continuation-in-part of Ser. No. 103,475, Oct. 1, 1987, abandoned, which is a continuation-in-part of Ser. No. 76,260, Jul. 21, 1987, abandoned, which is a continuation-in-part of Ser. No. 30,519, Mar. 27, 1987, abandoned.

[51] Int. Cl.$^5$ .................. A61K 31/70; C07H 17/00
[52] U.S. Cl. .................. 514/47; 514/48; 514/50; 514/51; 536/26.5
[58] Field of Search .................. 514/49, 50, 51, 46, 514/47; 536/27, 28, 29, 54

[56] References Cited

U.S. PATENT DOCUMENTS

| | | | |
|---|---|---|---|
| 3,280,104 | 10/1966 | Moffatt et al. | 536/23 |
| 3,317,512 | 5/1967 | Wechter | 536/27 |
| 3,397,268 | 8/1968 | Hunter | 536/27 |
| 3,457,253 | 7/1969 | Wechter | 536/27 |
| 3,817,982 | 6/1974 | Verheyden et al. | 536/23 |
| 4,594,415 | 6/1986 | Robins et al. | 536/27 |
| 4,724,232 | 2/1988 | Rideout et al. | 514/45 |
| 4,837,311 | 6/1989 | Tam et al. | 536/29 |
| 4,855,304 | 8/1989 | Devash | 536/27 |
| 4,981,957 | 1/1991 | Lebleu et al. | 536/27 |

OTHER PUBLICATIONS

Kochetkov et al., *Organic Chemistry of Nucleic Acids*, pp. 64–75 (Plenum Press 1971).
De Clercq, *Meth and Find. Exptl. Clin. Pharmacol.*, 2(5):253–257 (1980).
Yarchoan et al., *Lancet*, pp. 575–580 (1986).
Bone et al., *Chem. Abstracts*, 105:221543t (1986).
Baba et al., *Biochem Biophys. Res. Comm.*, 142: 128–134 (1987).
Herdewijn et al., *J. Med. Chem.*, 30:1270–1278 (1987).
Chu et al., *Tetrahedron Lett.*, 29:5349–5452 (1988).
Vince et al., *Biochem Biophys. Res. Comm.*, 156:1046–1053 (1988).
Mansuri et al., *J. Med. Chem.*, 32:461–466 (1989).
Mitsuya et al., *Proc. Natl. Acad. Sci. USA*, 83:1911–1915 (1986).
Balzarini et al., *Biochem. Biophys. Res. Comm.*, 140:735–742 (1986).
Dahlberg et al., *Proc. Natl. Acad. Sci. USA*, 84:2469–2473 (1987).

*Primary Examiner*—Johnnie R. Brown
*Assistant Examiner*—J. Oliver Wilson
*Attorney, Agent, or Firm*—Kirschstein, Ottinger, Israel & Schiffmiller

[57] ABSTRACT

Novel anti-viral compounds comprise phosphate-linked dimers of anti-viral nucleoside derivatives, or salts or esters of such nucleoside dimers. Pharmaceutical compositions containing the dimers and methods of treatment utilizing the same are disclosed.

10 Claims, No Drawings

ANTI-VIRAL COMPOUNDS, DOSAGE FORMS AND METHODS

CROSS-REFERENCE TO RELATED APPLICATIONS

This application is a continuation of application Ser. No. 07/638,335, filed Jan. 8, 1991, now abandoned, which is a continuation-in-part of co-pending application Ser. No. 07/319,680, filed Mar. 7, 1989, now abandoned, which is a continuation-in-part of Ser. No. 07/122,736, filed Nov. 19, 1987, now abandoned, which was a continuation-in-part of Ser. No. 07/103,475, filed Oct. 1, 1987, now abandoned, which was a continuation-in-part of Ser. No. 07/076,260, filed Jul. 21, 1987, now abandoned, which was a continuation-in-part of Ser. No. 07/030,519, filed Mar. 27, 1987, now abandoned.

BACKGROUND OF THE INVENTION

The starting materials of the present invention, 3'-azidothymidine (which may also be named 3'-deoxyazidothymidine or AZT) 2',3'-dideoxyadenosine (ddA), 2',3'-dideoxyinsine (ddI), 2',3'-didehydrodideoxycytidine (d4C), 2',3'-didehydro-3'-deoxythymidine (d4T), 3'-fluoro-3'-deoxythymidine (FLT), 3'-azido-2',3'-dideoxyuridine (AZddU), carbocyclic-2',3'-didehydrodideoxyguanosine (Carbovir), 2'-deoxy-3'-thiacytidine (DTC) and the 2'-fluoro analogs of ddA, ddI and 2',3'-dideoxycytidine (ddC) are known nucleoside derivatives having anti-viral activity. With the discovery and proliferation of contagious, serious, sexually transmitted viral afflictions, anti-viral medicaments of increasing potency are actively sought.

One method of increasing potency is to increase dosage. However, the limitations of this method are quickly surpassed due to considerations restricting the feasible size of the dosage. More importantly, the toxicity of such anti-viral agents as AZT severely limits the maximum dosage that can be safely administered. Compounds with a favorable ratio of toxic does to effective dose, for example as measured by their cytotherapeutic index ($ID_{50}/ED_{50}$), are required.

DETAILED DESCRIPTION OF THE INVENTION

The invention pertains to phosphate-linked or bridged dimers of anti-virally active nucleoside derivatives. The subject dimers have the following structural formula:

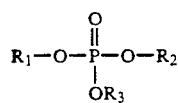

(I)

wherein $R_1$ and $R_2$ are each selected from the group consisting of the following:

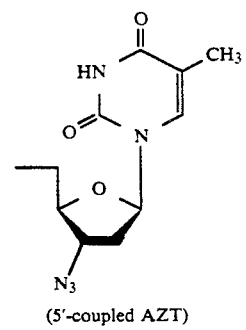

(5'-coupled AZT)

(a)

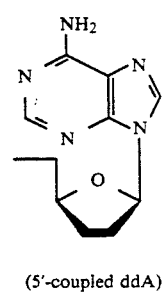

(5'-coupled ddA)

(b)

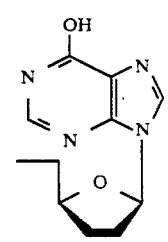

(5'-coupled ddI)

(c)

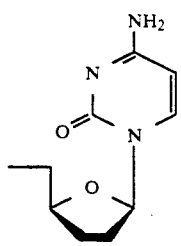

(5'-coupled d4C)

(d)

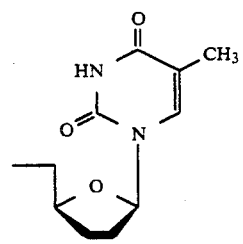

(5'-coupled d4T)

(e)

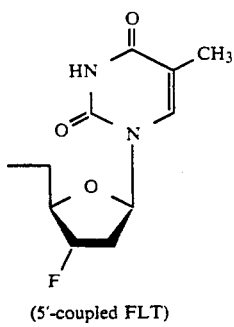

(5'-coupled FLT)

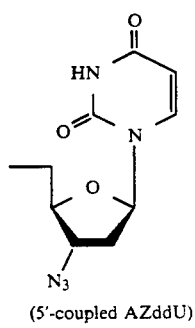

(5'-coupled AZddU)

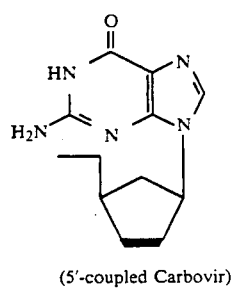

(5'-coupled Carbovir)

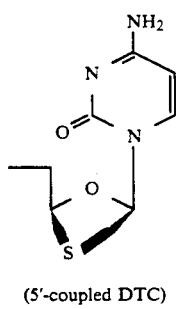

(5'-coupled DTC)

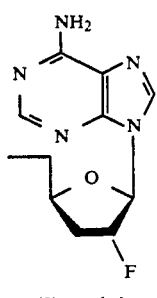

(5'-coupled 2'-fluoro-ddA)

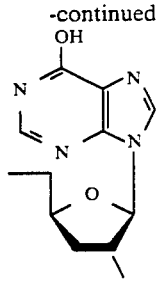

(5'-coupled 2'-fluoro-ddI)

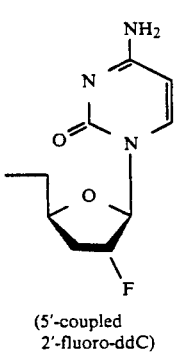

(5'-coupled 2'-fluoro-ddC)

and at least one of $R_1$, $R_2$ is not (a), and wherein $R_3$ is hydrogen, lower alkyl ($C_1$–$C_8$), substituted lower alkyl, haloalkyl, cyanoalkyl, aryl, aralkyl or substituted aryl or aralkyl.

Pharmaceutically acceptable salts of compounds of formula (I) are also comprehended by the present invention. As a pharmaceutically acceptable salt there is contemplated any salt of the compound which exhibits the anti-viral properties of the compound. For example, ammonium salts, metallic salts such as the sodium or magnesium salts, or organic anion salts such as pyridinium salts of compound I are contemplated by the present invention.

$R_1$ and $R_2$ may be the same or different 5'-coupled compounds selected from the above group; i.e., compound I may be a phosphate-bridged homodimer or heterodimer, but not (as noted previously) a homodimer of AZT.

As used herein, the phrase "5'-coupled compounds" refers to nucleoside derivatives whose 5'-hydroxyl group has been eliminated during the coupling or esterification reaction with the phosphate moiety.

The present invention also contemplates anti-viral pharmaceutical compositions for the oral delivery of a compound of formula (I) to a patient which include said compound in a pharmaceutically acceptable oral dosage vehicle or form, wherein said vehicle contains inert ingredients that do not interfere with the anti-viral activity of said compound.

Dosage forms for oral delivery may include conventional tablets, coated tablets, capsules, caplets, lozenges, liquids, elixirs or any other oral dosage form conventionally used in the pharmaceutical arts.

As pharmaceutically acceptable inert ingredients there are contemplated carriers, excipients, fillers, binders, solvents, etc. which do not interfere with the anti-viral activity of the active ingredient.

In addition, other pharmaceutical agents such as different anti-virals or other medicaments may be included in the dosage form of the present invention. Exemplary of suitable additional anti-viral compounds are amantadine hydrochloride, idoxuridine and methisazone.

Also, fillers such as clays or siliceous earth may be utilized if desired to adjust the size of the dosage form.

Further ingredients such as excipients and carriers may be necessary to impart the desired physical properties of the dosage form. Such physical properties are, for example, release rate, texture and size. Examples of excipients and carriers useful in oral dosage forms are waxes such as beeswax, castor wax, glycowax and carnauba wax, cellulose compounds such as methylcellulose, ethylcellulose, carboxymethylcellulose, cellulose acetate phthalate, hydroxypropylcellulose and hydroxypropylmethylcellulose, polyvinyl chloride, polyvinyl pyrrolidone, stearyl alcohol, glycerin monstearate, methacrylate compounds such as polymethacrylate, methyl methacrylate and ethylene glycol dimethacrylate, polyethylene glycol and hydrophilic gums.

A preferred embodiment of the pharmaceutical compositions of the present invention involves pharmaceutical dosage forms wherein the compound of formula (I) is present in an amount between about 50 and about 800 mg. The exact dosage for each patient will be a function of the physical characteristics of that patient such as body weight.

The invention also comprehends methods of providing anti-viral treatment to a patient in need of such treatment comprising the oral administration to the patient of a pharmaceutical composition containing a compound of formula (I), preferably from about 50 to about 800 mg of such compound, from one to about four times daily.

It has been discovered, unexpectedly, that compounds of formula (I) exhibit significantly greater anti-viral activity and/or lower toxicity (leading to a substantially better toxicity/activity ratio) than the nucleoside monomers which form the novel dimers, whether said monomers are administered alone or in combination. Radio-assay data indicate that a significant fraction of the novel compounds enters cells in intact (i.e., non-cleaved) form as dimers; the compounds are not merely cleaved in vivo into their substituent monomers.

The novel phosphate-linked dimers of the present invention may be prepared as follows:

1. A first dideoxynucleoside (an anti-virally active monomer) is reacted with cyanoethylphosphate, either in free form (such as 2-cyanoethylphosphate) or in the form of a salt (e.g., the ammonium salt), in the presence of a dehydration agent in accordance with the method of Tener, et al. (J. Amer. Chem. Soc., Vol. 83, p. 159, 1961) to form the cyanoethylphosphate ester of the first nucleoside derivative. The preferred dehydration agent for use in this step of the synthetic procedure is dicyclohexylcarbodiimide (DCC). Furthermore, in accordance with the procedure of Tener, et al., it is preferred that the reaction of cyanoethylphosphate with the nucleoside compound occur in anhydrous pyridine.

If desired, other phosphoric acid esters can be used as starting materials in this step in place of the cyanoethylphosphate—for example, 2,2,2-trichloroethylphosphate, phenylphosphate, p-chlorophenylphosphate, benzylphosphate, or p-nitrobenzylphosphate can be utilized. The nucleoside phosphate (or nucleotide) esters can also be prepared by reacting the corresponding nucleotide with an alcohol (e.g., 2-cyanoethanol) in the presence of DCC, or reacting the free nucleoside base with phosphoric acid esters in the presence of 2,4,5-triisopropylbenzenesulfonyl chloride (TPS).

2. The nucleoside cyanoethylphosphate (or other ester) produced by the preceding step is coupled to a second dideoxynucleoside monomer to form a phosphate triester internucleotide linkage using arysulfonyl chloride condensing agents such as, by way of example, TPS, mesitylenesulfonyl chloride or p-tolylsulfonyl chloride. The coupling reaction is carried out in the presence of a heterocyclic nitrogen-containing compound selected from the group consisting of pyrroles, imidazoles, triazoles, tetrazoles and pyridines. Preferred compounds include, by way of example, N-methylimidazole, 4-nitroimidazole, 1,2,4-triazole, 3-nitro 1,2,4-triazole, tetrazole or 4,4-dimethylaminopyridine.

Alternatively, acylating agents such as acetic anhydride, trimethylacetic anhydride (pivaloyl anhydride), pivaloyl chloride, benzoyl chloride, isobutyl chloroformate and diphenyl chlorophosphate or carbodiimides could also be used as condensing agents in the coupling reaction.

The coupling reaction can be carried out by dissolving the phosphate of the first nucleoside monomer and the second nucleoside monomer in a suitable solvent, e.g., distilled pyridine, adding the arylsulfonyl chloride and stirring for about thirty minutes. The heterocyclic nitrogen-containing compound is then added to activate the coupling reaction and the solution stirred at room temperature for approximately eighteen hours in a sealed flask. The resulting solution contains the cyanoethylphosphate triester of the first and second nucleoside monomers.

3. The solution resulting from step 2 is concentrated in vacuo at room temperature and an alkaline solution (e.g., 10–30% ammonium hydroxide or 0.1N–1.0N sodium hydroxide or lithium hydroxide) is added. The resulting suspension is stirred at room temperature for about eighteen hours, after which the insoluble solid is removed by filtration and the filtrate concentrated in vacuo at room temperature. The end product is isolated by flash chromatography using a silica gel. Preferably the silica gel is modified before use by soaking in a 10% magnesium acetate/methanol solution and, after removal of the solution by suction filtration, dried in an oven overnight. Before use, the modified silica gel column must be washed with methanol to remove the absorbed magnesium acetate.

The cyanoethyl group is removed by treatment with alkali and the resultant product is a salt of the phosphate-linked dimer, or phosphate diester, of the first nucleoside monomer and second monomer. If the free phosphate is desired, the product can be dissolved in mild acid and recovered, or passed through a suitable cationic exchange column.

As those skilled in the art will appreciate, the synthetic procedures set forth above may be varied in many respects in accordance with conventional materials, methods and procedures known to synthetic organic chemists. Any procedure which yields the dimerized compounds of formula (I) in substantially pure form may be utilized.

The following Examples provide detailed illustrations of the compounds, compositions and methods of the present invention for producing phosphate-linked dimers of nucleoside compounds. The Examples are not intended, however, to limit or restrict the scope of the invention in any way, and should not be construed as providing conditions, reagents, equipment or reaction parameters which must be utilized exclusively to practice the present invention.

EXAMPLE 1

AZT-ddA Phosphate Dimer

1. The Preparation of Azido-beta-thymidine-5'-cyanoethylphosphate

Cyanoethylphosphate, Barium Salt (5.0 g) was suspended in 50 ml of distilled water. To the solution, 5 g of Dowex 50×8-200 ion exchange resin was added and stirred until the salt was dissolved. The solution was passed through a column packed with 15 g of Dowex ion exchange resin and 100 ml of distilled water was used to wash the column. The aqueous solution was evaporated in vacuo. To the residue was added 15 ml of pyridine (KOH dried) and the solution was evaporated in vacuo. This procedure was repeated one more time. The residue was dissolved in 70 ml of distilled pyridine. To the solution, 2 g of AZT was added and stirred for 10 minutes, following by adding 6.18 g of dicyclohexylcarbodiimide and stirring at room temperature for 48 hours in a sealed flask.

10 ml of distilled water was added to the resulting solution and stirred for 30 minutes. The reaction mixture was concentrated in vacuo and 100 ml of distilled water was added to the residue. The insoluble solid was removed by filtration and the filtrate was concentrated in vacuo and purified by flash chromatography on silica gel eluted with chloroform, methanol and concentrated ammonium hydroxide (70:30:1) to give AZT cyanoethylphosphate in about 90% yield.

2. The Preparation of Azido-beta-thymidine-2',3'-Dideoxyadenosine Phosphate (Ammonium Salt)

(a) AZT cyanoethylphosphate (600 mg, 1.5 mmol) and 2',3'-dideoxyadenosine (352 mg, 1.5 mmol) were dissolved in 60 ml of distilled pyridine. To the solution, 1.21 g (4 mmol) of 2,4,6-triisopropylbenzenesulfonyl chloride was added and stirred for 30 min., following by adding 0.984 ml (12 mmol) of N-methylimidazole and stirring at room temperature for 18 hours in a sealed flask, yielding AZT-DDA cyanoethylphosphate triester in solution.

(b) The resulting solution was concentrated in vacuo at room temperature, 60 ml of 15% ammonium hydroxide solution was added and the suspension was stirred at room temperature for 18 hours in a sealed flask. The insoluble solid was removed by filtration and the filtrate was concentrated in vacuo at room temperature. The product was isolated by flash chromatography using 150 g of modified silica gel (see below). The column was eluted successively with 1 liter of chloroform/methanol (70:30), 1 liter of chloroform/methanol/conc. ammonium hydroxide (70:30:1) and 1 liter of chloroform/methanol/conc. ammonium hydroxide (70:30:5) to give 619 mg of azido-beta-thymidine-2',3'-dideoxyadenosine phosphate ammonium salt in 73% yield.

(c) The modified silica gel utilized in (b) was prepared by soaking silica gel, 60 Angstrom pore size, 35-75 micro-particle size, in 10% magnesium acetate/methanol solution for 10 minutes. The excess of magnesium acetate/methanol solution was removed by suction filtration. The modified silica gel was dried in an oven at 80° C. overnight. The column packed with the modified silica gel must be washed with methanol to remove the absorbed magnesium acetate before it is used for the separation of the reaction mixture.

EXAMPLE 2

AZT-ddI Phosphate Dimer

Azido-B-thymidine cyanoethylphosphate (800 mg, 2.0 mmol) prepared in accordance with Example 1 and dideoxyinosine (425 mg, 1.8 mmol) were dissolved in 150 ml of dried pyridine. To the solution, 1.31 g (6.0 mmol) of mesitylenesulfonyl chloride was added and stirred for 30 min. followed by the addition of 717 ul (9.0 mmol) of N-methyl-imidazole. The reaction was stirred at ambient temperature for 18 hours and then concentrated under vacuum at ambient temperature. The residue was added to 160 ml of 15% ammonium hydroxide solution and stirred at ambient temperature for 4 hours. The solution was concentrated under vacuum, and the residue was purified by flash chromatography on 250 g of silica gel and eluted with (a) 1 liter of 70:30:1 of chloroform:methanol:concentrated ammonium hydroxide solution, (b) 1 liter of 70:30:5 of chloroform:methanol:concentrated ammonium hydroxide solution and (c) 1 liter of 60:40:5 of chloroform: methanol:concentrated ammonium hydroxide solution to give azido-$\beta$-thymidine-2',3'-dideoxyinosine phosphate ammonium salt in 65% yield.

EXAMPLE 3 ddA-ddA Phosphate Homodimer

2',3'-dideoxyadenosine (68 mg; 0.28 mmol) and 4,5-dichloroimidazole (136 mg; 1 mmol) were dissolved in dry dimethyl formamide (1.4 ml) and added slowly to bis(pyrrolidino) methoxyphosphine (50 ul). The reaction was stirred at room temperature for 10 minutes after which time a solution of ddA (66 mg; 0.28 mmol) and 1H-tetrazole (63 mg; 0.9 mmole) in acetonitrile (5 ml) was added. The reaction was stirred an additional 10 minutes at room temperature and then cooled to −10°. A solution (2 ml) containing iodine (63 mg; 0.28 mmol) and lutidine (58 ul; 0.50 mmole) in tetrahydrofuran:water (2:1) was added to the cooled reaction and after stirring 10 minutes, the reaction was evaporated in vacuo. The residue was dissolved in 10% n-butanol in chloroform (2 ml) and a 5% solution of sodium bisulfite was added until the iodine color was discharged. The organic layer was separated and the aqueous phase was washed with chloroform:methanol (3:1). The combined organic extracts were dried over anhydrous sodium sulfate and evaporated in vacuo. The residue was purified on preparative thin layer chromatography using chloroform:methanol:ammonia as the solvent system. The product yield was 43 mg. Mass spectrum (fission fragment) gave a molecular ion at 532 with additional masses at 555 $(M+Na)^+$; 577 $(M+2Na-H)^+$; 599 $(M+3Na-2H)^+$; NMR (MeOH-d$^4$) has absorptions at 8.4, 5.45, 4.13, 3.46 and 2.1–2.3.

EXAMPLE 4

AZT-DTC Phosphate Dimer

Mesitylene sulfonyl chloride (0.072g, 0.33 mmole) was added to a stirred solution of AZT cyanoethylphosphate (0.08g, 0.20 mmole) and 2'-deoxy-3'-thiacytidine (0.03g, 0.13 mmole) in anhydrous pyridine (1 ml). The solution was stirred 15 minutes at room temperature, 1-methylimidazole (0.081g, 0.99 mmole) added and the reaction mixture stirred 24 hours at room temperature. The solution was concentrated in vacuo, the residue dissolved in 15% NH$_4$OH solution (3 ml), stirred 2 hours at room temperature and concentrated in vacuo. Preparative chromatography, eluting CHCl$_3$:MeOH:NH$_4$OH (70:30:5) afforded the dimer (0.045g, 61%) as an off-white solid.

EXAMPLE 5

400 mg of the compound of Example 1 is admixed with carboxymethylcellulose and sucrose. The resultant mixture is compressed into a tablet suitable for oral administration.

EXAMPLE 6

600 mg of the compound of Example 2 is admixed with polyethylene glycol and hydroxypropylcellulose. The resultant mixture is compressed into a tablet suitable for oral administration.

EXAMPLE 7

800 mg of the compound of Example 3 is admixed with methyl cellulose and glycerin monostearate. The resultant mixture is compressed into a tablet suitable for oral administration.

EXAMPLE 8

A patient requiring antiviral treatment is administered a tablet prepared in accordance with Examples 5, 6 or 7 from one to four times daily.

EXAMPLE 9

Anti-Viral and Cyctotoxicity Assays

Drugs

The test compounds included the AZT-ddA phosphate dimer (AZT-P-ddA) and AZT-ddI phosphate dimer (AZT-P-ddI) of Examples 1 and 2, respectively; AZT-ddA cyanoethylphosphate triester (AZT-P(CyE)-ddA); AZT; ddA; ddI; AZT-AZT phosphate dimer (AZT-P-AZT) (not within the scope of the invention); and an unreacted mixture of AZT and ddA.

Virus

An isolate of HIV (TM) was obtained from the culture supernatant of normal peripheral blood mononuclear cells infected with virus isolated from a patient with AIDS. Supernatant from H9 cells infected with HIV (TM) was aliquoted at peak reverse transcriptase activity and kept frozen at −85° C. until use. HIV (TM) infectivity assays using sequential fivefold dilutions (performed in quadruplicate) determined the infectious virus titer (Reed-Muench method) to be $10^{4.5}$ TC ID$_{50}$ per ml.

Cells

Target MT-2 cells (an HTLV-I immortalized CD4+lymphoblastoid cell line) were propagated in growth medium (D-MEM supplemented with 15% heat-inactivated fetal bovine serum, 2mM glutamine, and 1% penicillin-streptomycin).

Cytotoxicity studies

MT-2 cells ($2\times10^5$ cells per ml) were exposed to multiple drug concentrations (performed in triplicate). The medium was changed every 3–4 days, followed by the addition of fresh drug. Cell viability was determined by the trypan blue exclusion method and compared to controls without drug.

HIV infectivity assays

Target MT-2 cells were exposed to DEAE-dextran (25 ug/ml, Sigma) for 20 minutes, washed and infected with HIV (TM) (MOI=0.001) at 37° C. for 1 hour. MT-2 cells ($3\times10^5$ per ml) were placed in growth medium and transferred to a 24-well plastic tray followed by the addition of drug. The cells were carried at 37° C. in humidified air containing 5% CO$_2$ for 14 days. Every 3–4 days, the medium was changed and fresh drug added. At each change of medium, cells and supernatants were assayed for measures of HIV expression. Uninfected and infected MT-2 cells without exposure to drug were used as controls. All cultures were performed in triplicate on two sets of experiments.

RESULTS

Inhibition of syncytium formation

MT-2 cells were chosen because of their sensitivity to HIV infection with the formation of giant syncytia that are quantifiable. The cytopathic effect of HIV could be monitored as a function of the input virus inoculum. When MT-2 cells were monitored in a 14 day assay, a MOI of 0.001 gave rise to the formation of syncytia after 4 days (>400 per well) and peak reverse transcriptase levels by day 8.

To investigate the inhibitory effects of the drugs on HIV-induced syncytia formation, the nucleoside dimers were compared to their monomers and their combinations at multiple concentrations in a 4 day syncytium inhibition assay. Among the dimers, AZT-P-ddA and AZT-P(CyE)-ddA exerted the strongest protective effect against the development of HIV-induced syncytia. AZT-P-ddA and its cyanoethylphosphate derivative completely protected MT-2 cells from the formation of syncytia at a concentration of 0.5 uM. AZT required a concentration of 1 uM, ddA, 10 uM, and the combination of AZT+ddA, 0.5 uM to achieve full protection. No anti-HIV effects were seen at concentrations below 0.01 uM.

Cytotherapeutic evaluation

The comparative HIV inhibitory effects of nucleosides and the novel nucleoside dimers are shown on Table 1. The 50% inhibitory dose (ID$_{50}$) and 50% effective dose (ED$_{50}$) of each compound were calculated using linear regression analysis from the results of a 14 day assay that monitored cell viability and the expression of HIV antigen by cellular fluorescence.

The growth inhibitory effects of the compounds on MT-2 cells that were not exposed to the virus were compared. According to their ID$_{50}$, the compounds could be classified into three major groups. The compounds with the highest toxicity were AZT-P-AZT, AZT +ddA, and AZT. Compounds with moderate toxicity were AZT-P-ddA, AZT-P-ddI, and AZT-P (CyE)-ddA. The compounds with the least toxicity were ddI and ddA. When the cytotoxic effects of the compounds were tested against the human cell lines H9 and U937, similar toxicity profiles were seen.

The anti-HIV activity of the compounds according to their ED$_{50}$ revealed two major profiles. The most potent compounds were AZT+ddA, AZT-P-ddA, AZT-P(CyE)-dda, AZT-P-ddI, and AZT-P-AZT. AZT, ddA, and ddI exhibited weaker activities. However, the cytotherapeutic indices of AZT-P-ddA, AZT-P-ddI, and AZT-P(CyE)-ddA were the highest.

TABLE 1

| Comparative Inhibitory Effects of Compounds* | | |
|---|---|---|
| Drug | ID$_{50}$ (uM) | ED$_{50}$ (uM) | CTI |
| AZT | 100 | 4.0 | 25 |
| ddA | 400 | 7.0 | 57 |
| ddI | 450 | 7.5 | 60 |

TABLE 1-continued

| Comparative Inhibitory Effects of Compounds* | | | |
|---|---|---|---|
| Drug | ID$_{50}$ (uM) | ED$_{50}$ (uM) | CTI |
| AZT + ddA | 80 | 0.6 | 133 |
| AZT-P-AZT | 60 | 1.5 | 40 |
| AZT-P(CyE)-ddA | 210 | 0.7 | 300 |
| AZT-P-ddA | 200 | 0.8 | 250 |
| AZT-P-ddI | 240 | 1 | 240 |

*The results are expressed as the arithmetic mean of triplicate cultures from two sets of experiments. Linear regression analysis was used to determine the ID$_{50}$ and ED$_{50}$. ID$_{50}$, drug concentration required to reduce the number of uninfected MT-2 cells by 50% on day 14. ED$_{50}$, drug concentration achieving 50% inhibition of HIV expression assessed by immunofluorescence on day 14. CTI, cytotherapeutic index: ID$_{50}$/ED$_{50}$.

EXAMPLE 10

Reverse Transcriptase Assay

Reverse transcriptase (RT) has been shown to be involved in the replication of HIV (Mitsuya et al. 1987). The inhibition of RT by various agents is shown in Table 2. AZT-p-ddI at a concentration of 1 ug/ml inhibited the enzyme through at least 11 days whereas AZT at 1 ug/ml was effective at 7 days but not at 11 days. In this assay, the activity of AZT-P-ddA was comparable to that of AZT.

TABLE 2

| INHIBITION OF REVERSE TRANSCRIPTASE ACTIVITY* | | | |
|---|---|---|---|
| | EVALUATION PERIOD (DAYS) | | |
| DRUG | 7 | 11 | 14 |
| CONTROL (NO DRUG) | 11,000 | 38,000 | 34,000 |
| ddA (10 uM) | 500 | 3,000 | 4,500 |
| ddA (1 uM) | 5,500 | 45,000 | 39,500 |
| AZT-P-ddA (5 Ug/ml) | 500 | 500 | 500 |
| AZT-P-ddA (1 Ug/ml) | 1,500 | 12,000 | 26,500 |
| AZT (1 Ug/ml) | 1,500 | 12,000 | 23,500 |
| AZT (0.5 Ug/ml) | 2,000 | 16,500 | 28,000 |
| AZT-P(CyE)-ddA (5 Ug/ml) | 1,000 | 4,500 | 12,000 |
| AZT-P(CyE)-ddA (1 Ug/ml) | 6,000 | 43,000 | 36,000 |
| AZT-P-ddI (5 Ug/ml) | 1,000 | 1,500 | 25,000 |
| AZT-P-ddI (1 Ug/ml) | 1,000 | 3,000 | 10,000 |

*Target cells = H9 cells. MOI = 1.0. Media changes with the addition of fresh drug were performed at 3-4 day intervals. Results are expressed as CPM-Reverse Transcriptase activity per ml in culture supernatant. CPM >5,000 signifies abnormal elevations in Reverse Transcriptase activity. The results represent the mean of duplicate studies in one experiment.

The syntheses described in Examples 1, 2 and 4 above can be performed using any desired phosphoric acid ester to produce the nucleoside monomer phosphate ester (nucleotide ester) and subsequently the nucleoside dimer triester of formula (I). Thus, apart from cyanoethylphosphate, esters such as p-chlorophenylphosphate, 2,2,2-trichloroethylphosphate, p-nitrobenzylphosphate and the like can be utilized as starting materials to produce the corresponding nucleotide esters and nucleoside dimer triesters.

The triesters can themselves be used as active antiviral ingredients or can be further treated with alkali (MOH) to yield the corresponding diester salts, i.e., $R_1P(R_2)OO^-M^+$. These salts can be converted to the free dimer phosphates ($R_1P(R_2)OOH$) in mild acidic solution or through the use of suitable ion exchange resins.

It has thus been shown that there are provided compounds, compositions and methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims.

1. A compound having the formula

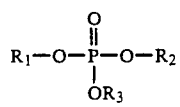

wherein $R_1$ is:

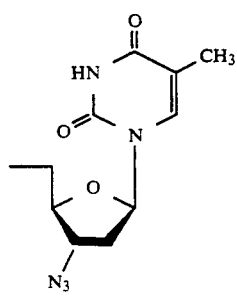

(a)

and $R_2$ is selected from the group consisting of:

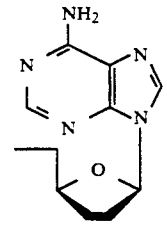

(b)

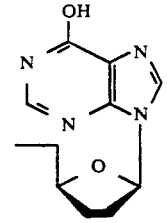

(c)

and

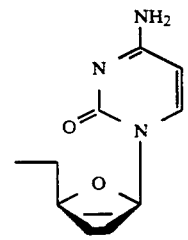

(d)

and wherein R₃ is selected from the group consisting of hydrogen, lower alkyl, substituted lower alkyl, haloalkyl, cyanoalkyl, aryl, aralkyl, substituted acryl and substituted aralkyl, or a pharmaceutically acceptable salt of said compound.

2. A compound according to claim 1 wherein R₂ is

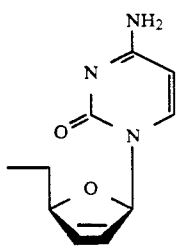

3. A compound according to claim 1 wherein R₂ is:

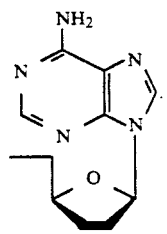

4. A compound according to claim 1 wherein R₂ is:

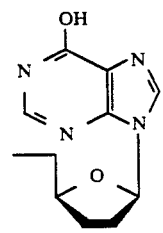

5. A compound according to claim 1 wherein R₃ is hydrogen.

6. A compound according to claim 1 wherein R₃ is cyanoethyl, 2,2,2-trichloroethyl, phenyl, p-chlorophenyl, benzyl or p-nitrobenzyl.

7. A pharmaceutical composition for oral administration to a patient requiring anti-viral treatment comprising a compound according to claim 1 in a pharmaceutically acceptable oral dosage form.

8. A composition according to claim 7 wherein said dosage form further comprises inert carriers, excipients, fillers, binders or solvents.

9. A composition according to claim 7 wherein said dosage form is a table, capsule, caplet, lozenge, liquid or elixir.

10. A composition according to claim 9 wherein said dosage form is a tablet.

* * * * *

UNITED STATES PATENT AND TRADEMARK OFFICE
CERTIFICATE OF CORRECTION

PATENT NO. : 5,187,163
DATED : February 16, 1993
INVENTOR(S) : Frost et al.

It is certified that error appears in the above-identified patent and that said Letters Patent is hereby corrected as shown below:

In col. 1, line 49, change "does" to --dose--.

In col. 6, line 4, change "arysulfonyl" to --arylsulfonyl--.

In col. 13, line 10, change "acryl" to --aryl--.

In col. 14, line 38, change "table" to --tablet--.

Signed and Sealed this

Fourteenth Day of December, 1993

Attest:

BRUCE LEHMAN

Attesting Officer   Commissioner of Patents and Trademarks